United States Patent
Colli et al.

(10) Patent No.: US 12,396,853 B2
(45) Date of Patent: Aug. 26, 2025

(54) SYSTEMS AND METHODS FOR DELIVERY OF CHORDAE REPLACEMENT SYSTEM

(71) Applicant: VALCARE MEDICAL, INC., Wilmington, DE (US)

(72) Inventors: Andrea Colli, Padua (IT); Nadav Yellin, Aven Yehuda (IL); Samuel Shaolian, Newport Beach, CA (US); Shuki Porath, Haifa (IL)

(73) Assignee: Valcare Medical, Inc., Wilmington, DE (US)

( * ) Notice: Subject to any disclaimer, the term of this patent is extended or adjusted under 35 U.S.C. 154(b) by 576 days.

(21) Appl. No.: 17/595,919

(22) PCT Filed: Jun. 11, 2020

(86) PCT No.: PCT/US2020/037296
§ 371 (c)(1),
(2) Date: Nov. 29, 2021

(87) PCT Pub. No.: WO2020/252202
PCT Pub. Date: Dec. 17, 2020

(65) Prior Publication Data
US 2022/0226117 A1    Jul. 21, 2022

Related U.S. Application Data

(60) Provisional application No. 62/859,968, filed on Jun. 11, 2019.

(51) Int. Cl.
*A61F 2/24* (2006.01)
*A61B 17/00* (2006.01)

(52) U.S. Cl.
CPC ...... *A61F 2/2466* (2013.01); *A61B 17/00234* (2013.01); *A61F 2/2457* (2013.01);
(Continued)

(58) Field of Classification Search
CPC .......... A61F 2/2466; A61F 2/2457; A61F 2220/0016; A61F 2220/0041;
(Continued)

(56) References Cited

U.S. PATENT DOCUMENTS

| 4,602,911 A | 7/1986 | Ahmadi et al. |
| 4,874,378 A | 10/1989 | Hillstead |

(Continued)

FOREIGN PATENT DOCUMENTS

| CN | 2114422 U | 9/1992 |
| CN | 2633218 Y | 8/2004 |

(Continued)

OTHER PUBLICATIONS

PCT/US2020/037296, International Search Report and Written Opinion, 7 pages, Sep. 10, 2020.
(Continued)

*Primary Examiner* — Melanie R Tyson
*Assistant Examiner* — Rachel S Highland
(74) *Attorney, Agent, or Firm* — Greenberg Traurig, LLP; Christopher C. Bolten; Robert D. Ward

(57) ABSTRACT

A system and method of repairing a native chordae of a patient using an artificial chordae. The artificial chordae is inserted into the patient in a non-deployed configuration using a delivery system and is delivered to a desired position within the patient. An operator causes the artificial chordae to transition from the non-deployed configuration to a deployed configuration. The artificial chordae is anchored to a myocardium of the patient. The artificial chordae is attached to a leaflet of the native chordae at an attachment location and tuned to a desired tension.

13 Claims, 23 Drawing Sheets

(52) U.S. Cl.
CPC .............. *A61B 2017/00243* (2013.01); *A61F 2220/0016* (2013.01); *A61F 2220/0041* (2013.01)

(58) Field of Classification Search
CPC ....... A61F 2250/0007; A61B 17/00234; A61B 2017/00243; A61B 17/122; A61B 2017/00783; A61B 2017/0404; A61B 2017/0406; A61B 2017/0417; A61B 2017/0437; A61B 2017/0441; A61B 2017/0464; A61B 2017/0495; A61B 2017/0496; A61B 17/0401; A61B 2017/0435; A61B 2017/0412; A61B 2017/0445; A61B 2017/0427

See application file for complete search history.

(56) References Cited

U.S. PATENT DOCUMENTS

| | | | |
|---|---|---|---|
| 4,953,540 A | 9/1990 | Ray et al. | |
| 5,080,662 A | 1/1992 | Paul | |
| 5,236,440 A | 8/1993 | Hlavacek | |
| 5,306,296 A | 4/1994 | Wright et al. | |
| 5,609,565 A | 3/1997 | Nakamura | |
| 5,695,518 A | 12/1997 | Laerum | |
| 5,716,370 A | 2/1998 | Williamson, IV et al. | |
| 5,855,614 A | 1/1999 | Stevens et al. | |
| 6,113,611 A | 9/2000 | Allen et al. | |
| 6,231,602 B1 | 5/2001 | Carpentier et al. | |
| 6,447,524 B1 | 9/2002 | Knodel et al. | |
| 6,619,291 B2 | 9/2003 | Hlavka et al. | |
| 6,629,534 B1 | 10/2003 | St. Goar et al. | |
| 6,669,687 B1 | 12/2003 | Saadat | |
| 6,689,048 B2 | 2/2004 | Vanden Hoek et al. | |
| 6,726,704 B1 | 4/2004 | Loshakove et al. | |
| 6,776,784 B2 | 8/2004 | Ginn | |
| 6,790,229 B1 | 9/2004 | Berreklouw | |
| 6,797,002 B2 | 9/2004 | Spence et al. | |
| 6,805,711 B2 | 10/2004 | Quijano et al. | |
| 6,869,444 B2 | 3/2005 | Gabbay | |
| 6,893,459 B1 | 5/2005 | MacOviak | |
| 7,101,395 B2 | 9/2006 | Tremulis et al. | |
| 7,114,953 B1 | 10/2006 | Wagner | |
| 7,175,660 B2 | 2/2007 | Cartledge et al. | |
| 7,238,191 B2 | 7/2007 | Bachmann | |
| 7,285,087 B2 | 10/2007 | Moaddeb et al. | |
| 7,297,150 B2 | 11/2007 | Cartledge et al. | |
| 7,569,072 B2 | 8/2009 | Berg et al. | |
| 7,594,887 B2 | 9/2009 | Moaddeb et al. | |
| 7,635,329 B2 | 12/2009 | Goldfarb et al. | |
| 7,655,040 B2 | 2/2010 | Douk et al. | |
| 7,717,954 B2 | 5/2010 | Solem et al. | |
| 7,722,668 B2 | 5/2010 | Moaddeb et al. | |
| 7,758,637 B2 | 7/2010 | Starksen et al. | |
| 7,828,819 B2 | 11/2010 | Webler et al. | |
| 7,837,729 B2 | 11/2010 | Gordon et al. | |
| 7,988,725 B2 | 8/2011 | Gross et al. | |
| 8,163,014 B2 | 4/2012 | Lane et al. | |
| 8,182,529 B2 | 5/2012 | Gordon et al. | |
| 8,236,049 B2 | 8/2012 | Rowe et al. | |
| 8,287,591 B2 | 10/2012 | Keidar et al. | |
| 8,333,204 B2 * | 12/2012 | Saadat | A61B 18/1442 606/232 |
| 8,518,107 B2 | 8/2013 | Tsukashima et al. | |
| 8,579,968 B1 | 11/2013 | Shannon et al. | |
| 8,690,939 B2 * | 4/2014 | Miller | A61F 2/2457 623/2.11 |
| 8,821,570 B2 | 9/2014 | DuMontelle et al. | |
| 9,180,008 B2 | 11/2015 | Yellin et al. | |
| 9,402,721 B2 | 8/2016 | Buchbinder et al. | |
| 9,433,503 B2 | 9/2016 | Tsukashima et al. | |
| 9,839,519 B2 | 12/2017 | Shaolian et al. | |
| 9,877,833 B1 | 1/2018 | Bishop et al. | |
| 10,405,979 B2 * | 9/2019 | Schaffner | A61B 17/0469 |
| 10,543,087 B2 | 1/2020 | Yellin et al. | |
| 10,779,945 B2 | 9/2020 | Buchbinder et al. | |
| 11,058,417 B2 | 7/2021 | Foerster et al. | |
| 11,191,536 B2 | 12/2021 | Foerster et al. | |
| 11,224,422 B2 | 1/2022 | Foerster et al. | |
| 11,298,230 B2 | 4/2022 | Shaolian et al. | |
| 11,382,749 B2 | 7/2022 | Yellin et al. | |
| 11,510,835 B2 | 11/2022 | Yellin et al. | |
| 11,534,300 B2 | 12/2022 | Yellin et al. | |
| 11,571,301 B2 | 2/2023 | Yellin et al. | |
| 11,571,307 B2 | 2/2023 | Yellin et al. | |
| 11,576,779 B2 | 2/2023 | Yellin et al. | |
| 11,617,647 B2 | 4/2023 | Yellin | |
| 11,654,018 B2 | 5/2023 | Shaolian et al. | |
| 11,793,628 B2 | 10/2023 | Dumontelle et al. | |
| 11,806,009 B2 | 11/2023 | Foerster et al. | |
| 11,806,237 B2 | 11/2023 | Rozen et al. | |
| 11,813,164 B2 | 11/2023 | Yellin et al. | |
| 11,857,418 B2 | 1/2024 | Yellin et al. | |
| 12,115,069 B2 | 10/2024 | Shaolian et al. | |
| 12,127,941 B2 | 10/2024 | Yellin et al. | |
| 2002/0151961 A1 | 10/2002 | Lashinski et al. | |
| 2002/0151970 A1 | 10/2002 | Garrison et al. | |
| 2002/0188170 A1 * | 12/2002 | Santamore | A61K 9/14 623/23.64 |
| 2002/0198526 A1 | 12/2002 | Shaolian et al. | |
| 2003/0050649 A1 | 3/2003 | Brock et al. | |
| 2003/0050693 A1 | 3/2003 | Quijano et al. | |
| 2003/0078465 A1 | 4/2003 | Pai et al. | |
| 2003/0078671 A1 | 4/2003 | Lesniak et al. | |
| 2003/0191528 A1 | 10/2003 | Quijano et al. | |
| 2003/0198605 A1 | 10/2003 | Montgomery | |
| 2003/0199974 A1 | 10/2003 | Lee et al. | |
| 2004/0044364 A1 | 3/2004 | DeVries et al. | |
| 2004/0068276 A1 | 4/2004 | Golden et al. | |
| 2004/0073237 A1 | 4/2004 | Leinsing | |
| 2004/0122514 A1 | 6/2004 | Fogarty et al. | |
| 2004/0138744 A1 | 7/2004 | Lashinski et al. | |
| 2004/0148021 A1 | 7/2004 | Cartledge et al. | |
| 2004/0193191 A1 | 9/2004 | Starksen et al. | |
| 2004/0243230 A1 | 12/2004 | Navia et al. | |
| 2004/0249391 A1 | 12/2004 | Cummins | |
| 2004/0260393 A1 | 12/2004 | Rahdert et al. | |
| 2004/0260394 A1 | 12/2004 | Douk et al. | |
| 2005/0004668 A1 | 1/2005 | Aklog et al. | |
| 2005/0020696 A1 | 1/2005 | Montgomery et al. | |
| 2005/0033325 A1 | 2/2005 | May et al. | |
| 2005/0065550 A1 | 3/2005 | Starksen et al. | |
| 2005/0090846 A1 | 4/2005 | Pedersen et al. | |
| 2005/0096740 A1 | 5/2005 | Langberg et al. | |
| 2005/0113910 A1 | 5/2005 | Paniagua et al. | |
| 2005/0137692 A1 | 6/2005 | Haug et al. | |
| 2005/0137695 A1 | 6/2005 | Salahieh et al. | |
| 2005/0203549 A1 | 9/2005 | Realyvasquez | |
| 2005/0222678 A1 | 10/2005 | Lashinski et al. | |
| 2005/0240200 A1 | 10/2005 | Bergheim | |
| 2005/0250161 A1 | 11/2005 | Suciu-Foca et al. | |
| 2005/0267572 A1 | 12/2005 | Schoon et al. | |
| 2005/0283190 A1 | 12/2005 | Huitema et al. | |
| 2005/0288778 A1 | 12/2005 | Shaoulian et al. | |
| 2005/0288781 A1 | 12/2005 | Moaddeb et al. | |
| 2006/0009737 A1 | 1/2006 | Whiting et al. | |
| 2006/0020327 A1 | 1/2006 | Lashinski et al. | |
| 2006/0052867 A1 | 3/2006 | Revuelta et al. | |
| 2006/0122633 A1 | 6/2006 | To et al. | |
| 2006/0129025 A1 | 6/2006 | Levine et al. | |
| 2006/0155165 A1 | 7/2006 | Vanden Hoek et al. | |
| 2006/0161169 A1 | 7/2006 | Nieminen et al. | |
| 2006/0184240 A1 | 8/2006 | Jimenez et al. | |
| 2006/0184242 A1 | 8/2006 | Lichtenstein | |
| 2006/0195134 A1 | 8/2006 | Crittenden | |
| 2006/0195135 A1 | 8/2006 | Navia et al. | |
| 2006/0241748 A1 | 10/2006 | Lee et al. | |
| 2006/0282161 A1 | 12/2006 | Huynh et al. | |
| 2007/0016287 A1 | 1/2007 | Cartledge et al. | |
| 2007/0027533 A1 | 2/2007 | Douk | |
| 2007/0038296 A1 | 2/2007 | Navia | |
| 2007/0051377 A1 | 3/2007 | Douk et al. | |
| 2007/0067027 A1 | 3/2007 | Moaddeb et al. | |

(56) References Cited

U.S. PATENT DOCUMENTS

| | | |
|---|---|---|
| 2007/0073098 A1 | 3/2007 | Lenker et al. |
| 2007/0080188 A1 | 4/2007 | Spence et al. |
| 2007/0093854 A1 | 4/2007 | Kayan |
| 2007/0118215 A1 | 5/2007 | Moaddeb |
| 2007/0128132 A1 | 6/2007 | Piergallini et al. |
| 2007/0135913 A1 | 6/2007 | Moaddeb et al. |
| 2007/0142907 A1 | 6/2007 | Moaddeb et al. |
| 2007/0213812 A1 | 9/2007 | Webler et al. |
| 2007/0233239 A1 | 10/2007 | Navia et al. |
| 2007/0239272 A1 | 10/2007 | Navia et al. |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0250161 A1 | 10/2007 | Dolan |
| 2007/0293942 A1 | 12/2007 | Mirzaee |
| 2008/0039934 A1 | 2/2008 | Styrc |
| 2008/0051807 A1 | 2/2008 | St. Goar et al. |
| 2008/0065011 A1 | 3/2008 | Marchand et al. |
| 2008/0177380 A1 | 7/2008 | Starksen et al. |
| 2008/0177381 A1 | 7/2008 | Navia et al. |
| 2008/0200980 A1 | 8/2008 | Robin et al. |
| 2008/0208327 A1 | 8/2008 | Rowe |
| 2008/0215145 A1 | 9/2008 | Moaddeb et al. |
| 2008/0243220 A1 | 10/2008 | Barker |
| 2008/0262513 A1 | 10/2008 | Stahler et al. |
| 2008/0262609 A1 | 10/2008 | Gross et al. |
| 2008/0288060 A1 | 11/2008 | Kaye et al. |
| 2008/0306586 A1 | 12/2008 | Cartledge et al. |
| 2009/0076599 A1 | 3/2009 | Bergin |
| 2009/0088838 A1 | 4/2009 | Shaolian et al. |
| 2009/0118747 A1 | 5/2009 | Bettuchi et al. |
| 2009/0125098 A1 | 5/2009 | Chuter |
| 2009/0149872 A1 | 6/2009 | Gross et al. |
| 2009/0216322 A1 | 8/2009 | Le et al. |
| 2009/0222083 A1 | 9/2009 | Nguyen et al. |
| 2009/0238778 A1 | 9/2009 | Mordas et al. |
| 2009/0299470 A1 | 12/2009 | Rao et al. |
| 2010/0010616 A1 | 1/2010 | Drews et al. |
| 2010/0030014 A1 | 2/2010 | Ferrazzi |
| 2010/0063586 A1 | 3/2010 | Hasenkam et al. |
| 2010/0076549 A1 | 3/2010 | Keidar et al. |
| 2010/0121433 A1 | 5/2010 | Bolling et al. |
| 2010/0161047 A1 | 6/2010 | Cabiri |
| 2010/0185274 A1 | 7/2010 | Moaddeb et al. |
| 2010/0191327 A1 | 7/2010 | Lane et al. |
| 2010/0204713 A1 | 8/2010 | Ruiz Morales |
| 2010/0211166 A1 | 8/2010 | Miller et al. |
| 2010/0249920 A1 | 9/2010 | Bolling et al. |
| 2010/0262232 A1 | 10/2010 | Annest |
| 2010/0266989 A1 | 10/2010 | Piergallini et al. |
| 2010/0280604 A1 | 11/2010 | Zipory et al. |
| 2010/0280605 A1 | 11/2010 | Hammer et al. |
| 2010/0286767 A1 | 11/2010 | Zipory et al. |
| 2011/0004299 A1 | 1/2011 | Navia et al. |
| 2011/0011917 A1 | 1/2011 | Loulmet |
| 2011/0022168 A1 | 1/2011 | Cartledge |
| 2011/0027753 A1 | 2/2011 | Maurat et al. |
| 2011/0034953 A1 | 2/2011 | Milo |
| 2011/0034999 A1 | 2/2011 | Carpentier et al. |
| 2011/0060407 A1* | 3/2011 | Ketai ................ A61B 17/0644 |
| | | 623/2.37 |
| 2011/0066231 A1 | 3/2011 | Cartledge et al. |
| 2011/0093062 A1 | 4/2011 | Cartledge et al. |
| 2011/0106245 A1 | 5/2011 | Miller et al. |
| 2011/0106247 A1 | 5/2011 | Miller et al. |
| 2011/0137397 A1 | 6/2011 | Chau et al. |
| 2011/0166649 A1 | 7/2011 | Gross et al. |
| 2011/0190879 A1 | 8/2011 | Bobo et al. |
| 2011/0208295 A1 | 8/2011 | Cartledge et al. |
| 2011/0208298 A1 | 8/2011 | Tuval et al. |
| 2011/0224785 A1 | 9/2011 | Hacohen |
| 2011/0257728 A1 | 10/2011 | Kuehn |
| 2011/0282361 A1 | 11/2011 | Miller et al. |
| 2011/0301698 A1 | 12/2011 | Miller et al. |
| 2011/0301699 A1 | 12/2011 | Saadat |
| 2011/0319989 A1 | 12/2011 | Lane et al. |
| 2012/0022557 A1 | 1/2012 | Cabiri et al. |
| 2012/0022639 A1* | 1/2012 | Hacohen ............... A61F 2/2436 |
| | | 623/2.11 |
| 2012/0022644 A1 | 1/2012 | Reich et al. |
| 2012/0059458 A1 | 3/2012 | Buchbinder et al. |
| 2012/0083806 A1* | 4/2012 | Goertzen ............ A61B 17/0401 |
| | | 606/151 |
| 2012/0083880 A1 | 4/2012 | Rankin et al. |
| 2012/0095455 A1 | 4/2012 | Rodmond et al. |
| 2012/0123531 A1* | 5/2012 | Tsukashima .......... A61F 2/2448 |
| | | 623/2.37 |
| 2012/0136436 A1 | 5/2012 | Cabiri et al. |
| 2012/0136463 A1 | 5/2012 | Muniz |
| 2012/0165930 A1 | 6/2012 | Gifford, III et al. |
| 2012/0245604 A1 | 9/2012 | Tegzes |
| 2012/0310330 A1 | 12/2012 | Buchbinder et al. |
| 2013/0066342 A1 | 3/2013 | Dell et al. |
| 2013/0087598 A1 | 4/2013 | Surti |
| 2013/0116780 A1 | 5/2013 | Miller et al. |
| 2013/0166022 A1 | 6/2013 | Conklin |
| 2013/0204361 A1 | 8/2013 | Adams et al. |
| 2013/0226289 A1* | 8/2013 | Shaolian ............... A61F 2/2448 |
| | | 623/2.37 |
| 2013/0226290 A1 | 8/2013 | Yellin et al. |
| 2013/0282114 A1 | 10/2013 | Schweich, Jr. et al. |
| 2013/0289718 A1 | 10/2013 | Tsukashima et al. |
| 2013/0289720 A1 | 10/2013 | Dobrilovic |
| 2013/0304197 A1 | 11/2013 | Buchbinder et al. |
| 2014/0005778 A1 | 1/2014 | Buchbinder et al. |
| 2014/0025163 A1 | 1/2014 | Padala et al. |
| 2014/0046433 A1 | 2/2014 | Kovalsky |
| 2014/0058505 A1 | 2/2014 | Bielefeld |
| 2014/0114407 A1 | 4/2014 | Rajamannan |
| 2014/0188130 A1 | 7/2014 | Sanchez et al. |
| 2014/0214157 A1 | 7/2014 | Börtlein et al. |
| 2014/0277411 A1 | 9/2014 | Börtlein et al. |
| 2014/0364939 A1 | 12/2014 | Deshmukh et al. |
| 2015/0073420 A1 | 3/2015 | Bookwalter et al. |
| 2015/0112432 A1 | 4/2015 | Reich et al. |
| 2015/0127093 A1 | 5/2015 | Hosmer et al. |
| 2015/0173897 A1 | 6/2015 | Raanani et al. |
| 2015/0173987 A1 | 6/2015 | Albinmousa et al. |
| 2015/0351903 A1 | 12/2015 | Morriss et al. |
| 2015/0366666 A1 | 12/2015 | Khairkhahan et al. |
| 2016/0022419 A1 | 1/2016 | Yellin et al. |
| 2016/0038286 A1 | 2/2016 | Yellin et al. |
| 2016/0089235 A1 | 3/2016 | Yellin |
| 2016/0100897 A1 | 4/2016 | Avalos et al. |
| 2016/0106420 A1 | 4/2016 | Foerster et al. |
| 2016/0120642 A1 | 5/2016 | Shaolian et al. |
| 2016/0120645 A1 | 5/2016 | Alon |
| 2016/0220371 A1 | 8/2016 | Keane |
| 2016/0270911 A1 | 9/2016 | Ganesan et al. |
| 2016/0331534 A1 | 11/2016 | Buchbinder et al. |
| 2017/0042670 A1 | 2/2017 | Shaolian et al. |
| 2017/0231763 A1 | 8/2017 | Yellin |
| 2017/0258590 A1 | 9/2017 | Khairkhahan |
| 2017/0296340 A1 | 10/2017 | Gross et al. |
| 2017/0325948 A1 | 11/2017 | Wallace et al. |
| 2018/0028387 A1 | 2/2018 | Yellin et al. |
| 2018/0042723 A1 | 2/2018 | Yellin et al. |
| 2018/0098849 A1 | 4/2018 | Yellin et al. |
| 2018/0161160 A1 | 6/2018 | Shaolian et al. |
| 2018/0161161 A1 | 6/2018 | Yellin et al. |
| 2018/0228610 A1 | 8/2018 | Lashinski et al. |
| 2018/0235758 A1 | 8/2018 | Biadillah et al. |
| 2018/0325670 A1 | 11/2018 | De Canniere |
| 2019/0053905 A1 | 2/2019 | Alon |
| 2019/0083091 A1 | 3/2019 | Foerster et al. |
| 2019/0083092 A1 | 3/2019 | Foerster et al. |
| 2019/0083239 A1 | 3/2019 | Shaolian et al. |
| 2019/0083240 A1 | 3/2019 | Shaolian et al. |
| 2019/0091022 A1 | 3/2019 | Yellin et al. |
| 2019/0133765 A1 | 5/2019 | Yellin et al. |
| 2020/0069426 A1* | 3/2020 | Conklin ................ A61F 2/2487 |
| 2020/0163763 A1 | 5/2020 | Zipory et al. |
| 2020/0170799 A1 | 6/2020 | Yellin et al. |

(56) References Cited

U.S. PATENT DOCUMENTS

| | | |
|---|---|---|
| 2020/0330228 A1 | 10/2020 | Anderson et al. |
| 2021/0085463 A1 | 3/2021 | Yellin et al. |
| 2021/0161662 A1 | 6/2021 | Albes |
| 2021/0353417 A1 | 11/2021 | Yellin et al. |
| 2022/0226116 A1 | 7/2022 | Colli et al. |
| 2022/0226771 A1 | 7/2022 | Lipscomb |
| 2023/0040083 A1 | 2/2023 | Gifford, III et al. |
| 2023/0045532 A1 | 2/2023 | Galler et al. |
| 2023/0372086 A1 | 11/2023 | Galler et al. |

FOREIGN PATENT DOCUMENTS

| | | |
|---|---|---|
| CN | 101411632 A | 4/2009 |
| CN | 101460113 A | 6/2009 |
| CN | 101553190 A | 10/2009 |
| CN | 102014797 A | 4/2011 |
| CN | 102088930 A | 6/2011 |
| CN | 202859386 U | 4/2013 |
| CN | 103179920 A | 6/2013 |
| CN | 103237523 A | 8/2013 |
| CN | 103735337 A | 4/2014 |
| CN | 203954080 U | 11/2014 |
| CN | 108618871 A | 10/2018 |
| CN | 113855324 A | 12/2021 |
| DE | 102014102653 A1 | 9/2015 |
| EP | 1752115 A1 | 2/2007 |
| EP | 2471464 A1 | 7/2012 |
| EP | 2600799 A2 | 6/2013 |
| EP | 2928538 A1 | 10/2015 |
| EP | 2967700 A1 | 1/2016 |
| EP | 2600799 B1 | 5/2017 |
| EP | 3213715 A1 | 9/2017 |
| EP | 2928538 B1 | 11/2018 |
| FR | 2845889 A1 | 4/2004 |
| GB | 1496804 A | 1/1978 |
| GB | 2366319 A | 3/2002 |
| KR | 20040095482 A | 11/2004 |
| RU | 125062 U1 | 2/2013 |
| WO | WO-8000673 A1 | 4/1980 |
| WO | WO-9009153 A1 | 8/1990 |
| WO | WO-9728745 A1 | 8/1997 |
| WO | WO-03017874 A1 | 3/2003 |
| WO | WO-03047467 A1 | 6/2003 |
| WO | WO-2005046488 A2 | 5/2005 |
| WO | WO-2007035882 A2 | 3/2007 |
| WO | WO-2008097999 A2 | 8/2008 |
| WO | WO-2009052427 A1 | 4/2009 |
| WO | WO-2009120764 A2 | 10/2009 |
| WO | WO-2010004546 A1 | 1/2010 |
| WO | WO-2010085659 A1 | 7/2010 |
| WO | WO-2011011443 A2 | 1/2011 |
| WO | WO-2011097355 A2 | 8/2011 |
| WO | 2011154942 A2 | 12/2011 |
| WO | WO-2012004679 A2 | 1/2012 |
| WO | WO-2012019052 A2 | 2/2012 |
| WO | WO-2012038550 A1 | 3/2012 |
| WO | 2012040865 A1 | 4/2012 |
| WO | WO-2012063228 A1 | 5/2012 |
| WO | WO-2012095159 A2 | 7/2012 |
| WO | WO-2012106354 A1 | 8/2012 |
| WO | WO-2012167095 A2 | 12/2012 |
| WO | WO-2013095816 A1 | 6/2013 |
| WO | WO-2013128436 A1 | 9/2013 |
| WO | WO-2013130641 A1 | 9/2013 |
| WO | WO-2013175468 A2 | 11/2013 |
| WO | WO-2014089424 A1 | 6/2014 |
| WO | WO-2014145399 A1 | 9/2014 |
| WO | WO-2014178869 A1 | 11/2014 |
| WO | WO-2014189509 A1 | 11/2014 |
| WO | WO-2014190329 A1 | 11/2014 |
| WO | WO-2014210600 A2 | 12/2014 |
| WO | WO-2015052629 A1 | 4/2015 |
| WO | WO-2015132668 A1 | 9/2015 |
| WO | WO-2016025894 A1 | 2/2016 |
| WO | WO-2016040526 A1 | 3/2016 |
| WO | WO-2018035118 A1 | 2/2018 |
| WO | WO-2018071540 A1 | 4/2018 |
| WO | WO-2018170424 A1 | 9/2018 |
| WO | WO-2020117842 A1 | 6/2020 |
| WO | WO-2020252200 A1 | 12/2020 |

OTHER PUBLICATIONS

Extended European Search Report for European Application No. 11815347.7, mailed Mar. 14, 2016, 10 Pages.
Extended European Search Report for European Application No. 12793292.9, mailed Dec. 1, 2014, 6 Pages.
Extended European Search Report for European Application No. 13755441.6, mailed Mar. 1, 2016, 12 Pages.
Extended European Search Report for European Application No. 13860442.6, mailed Aug. 11, 2016, 7 pages.
Extended European Search Report for European Application No. 13885021.9, mailed Jan. 3, 2017, 8 Pages.
Extended European Search Report for European Application No. 14762806.9, mailed Jul. 29, 2016, 7 Pages.
Extended European Search Report for European Application No. 14801009.3, mailed Dec. 5, 2016, 8 Pages.
Extended European Search Report for European Application No. 14817662.1, mailed Jan. 23, 2017, 7 Pages.
Extended European Search Report for European Application No. 17155803.4, mailed Aug. 9, 2017, 10 Pages.
Extended European Search Report for European Application No. 17835256.3, mailed Feb. 12, 2020, 9 Pages.
Extended European Search Report for European Application No. 17841988.3, mailed Dec. 16, 2019, 8 Pages.
Extended European Search Report for European Application No. 17860901.2, mailed Jun. 5, 2020, 06 Pages.
Extended European Search Report for European Application No. 18768197.8, mailed Oct. 19, 2020, 7 Pages.
Extended European Search Report for European Application No. 19151726.7, mailed Jul. 22, 2019, 9 Pages.
Extended European Search Report for European Application No. 19170261.2, mailed Aug. 5, 2019, 9 pages.
Extended European Search Report for European Application No. 19893113.1, mailed Nov. 17, 2022, 7 Pages.
Extended European Search Report for European Application No. 20206790.6, mailed Dec. 7, 2020, 9 Pages.
Extended European Search Report for European Application No. 20209605.3, mailed Mar. 9, 2021, 7 pages.
Extended European Search Report for European Application No. 20823198.5, mailed May 15, 2023, 15 Pages.
Extended European Search Report for European Application No. 20823682.8, mailed Apr. 14, 2023, 10 Pages.
Extended European Search Report for European Application No. 20841346.8, mailed Jul. 21, 2023, 9 Pages.
International Search Report and Written Opinion for International Application No. PCT/IL2022/050868, mailed Nov. 17, 2022, 19 Pages.
International Search Report and Written Opinion for International Application No. PCT/IL2023/050527, mailed Aug. 8, 2023, 14 Pages.
International Search Report and Written Opinion for International Application No. PCT/US2011/046659, mailed Jun. 4, 2012, 13 Pages.
International Search Report and Written Opinion for International Application No. PCT/US2012/040481, mailed Dec. 6, 2012, 12 Pages.
International Search Report and Written Opinion for International Application No. PCT/US2013/028065, mailed Jun. 27, 2013, 11 Pages.
International Search Report and Written Opinion for International Application No. PCT/US2013/042275, mailed Feb. 20, 2014, 18 Pages.
International Search Report and Written Opinion for International Application No. PCT/US2013/058102, mailed Apr. 21, 2014, 10 Pages.

(56) References Cited

OTHER PUBLICATIONS

International Search Report and Written Opinion for International Application No. PCT/US2013/073552, mailed Mar. 6, 2014, 10 Pages.
International Search Report and Written Opinion for International Application No. PCT/US2014/030163, mailed Aug. 27, 2014, 10 Pages.
International Search Report and Written Opinion for International Application No. PCT/US2014/039454, mailed Oct. 22, 2014, 11 Pages.
International Search Report and Written Opinion for International Application No. PCT/US2014/044920, mailed Dec. 24, 2014, 15 Pages.
International Search Report and Written Opinion for International Application No. PCT/US2017/044129, mailed Sep. 27, 2017, 9 Pages.
International Search Report and Written Opinion for International Application No. PCT/US2017/046933, mailed Dec. 21, 2017, 11 Pages.
International Search Report and Written Opinion for International Application No. PCT/US2017/056138, mailed Jan. 8, 2018, 6 Pages.
International Search Report and Written Opinion for International Application No. PCT/US2018/022910, mailed May 23, 2018, 7 Pages.
International Search Report and Written Opinion for International Application No. PCT/US2019/064289, mailed Feb. 5, 2020, 8 Pages.
International Search Report and Written Opinion for International Application No. PCT/US2020/037294, mailed Aug. 28, 2020, 8 Pages.
International Search Report and Written Opinion for International Application No. PCT/US2020/042201, mailed Oct. 9, 2020, 7 Pages.
International Search Report and Written Opinion for International Application No. PCT/US2021/071467, mailed Jan. 14, 2022, 12 Pages.
International Search Report and Written Opinion for International Application No. PCT/US2021/071468, mailed Jan. 19, 2022, 8 Pages.
Partial Supplementary European Search Report for European Application No. 11815347.7, mailed Nov. 16, 2015, 06 Pages.
Partial Supplementary European Search Report for European Application No. 13755441.6, mailed Nov. 3, 2015, 7 Pages.
International Search Report & Written Opinion dated Jul. 24, 2024 in Int'l PCT Patent Appl. Serial No. PCT/US2024/019797.

* cited by examiner

SYSTEMS AND METHODS FOR DELIVERY OF CHORDAE REPLACEMENT SYSTEM

PRIORITY

The present application is a national stage filing under 35 U.S.C. § 371 of International Patent Application No. PCT/US2020/037296, filed Jun. 11, 2020, which claims priority under 35 U.S.C. § 119 (e) to U.S. Provisional Patent Application No. 62/859,968, filed on Jun. 11, 2019, titled "SYSTEMS AND METHODS FOR DELIVERY OF CHORDEA REPLACEMENT SYSTEM," each of which is hereby incorporated by reference herein in its entirety.

BACKGROUND

The present invention relates to implantable devices. The invention is particularly useful in devices implantable by catheter for the treatment of mitral or tricuspid regurgitation. The cause of the regurgitation can be functional, degenerative, or any other reason. The invention could be used for valvular lesions as well.

Mitral regurgitation is a valvular dysfunction that causes blood volume to flow during systole (i.e., left ventricular contraction) from the left ventricle to the left atrium, in contrast to a healthy heart where this direction of flow is blocked by the mitral valve. The reversed flow during systole causes a rise in pressure in the left atrium. Maintaining a normal cardiac output results in increased left ventricle pressure.

Treating patients with mitral or tricuspid regurgitation could require valve repair or replacement in order to reduce or eliminate the regurgitation. For many years, the commonly accepted treatment was surgical repair or replacement of the native valve during open heart surgery. Valve repair is a procedure that may require complementary treatments such as utilizing annuloplasty rings with or without leaflet or chordae repair. In recent years, a trans vascular technique has been developed for introducing these devices in general and implanting an artificial chorda through a catheter in a manner that is less invasive than open heart surgery.

BRIEF DESCRIPTION OF THE DRAWINGS

Aspects, features, benefits and advantages of the embodiments described herein will be apparent with regard to the following description, appended claims, and accompanying drawings where:

DETAILED DESCRIPTION

Figure 1:
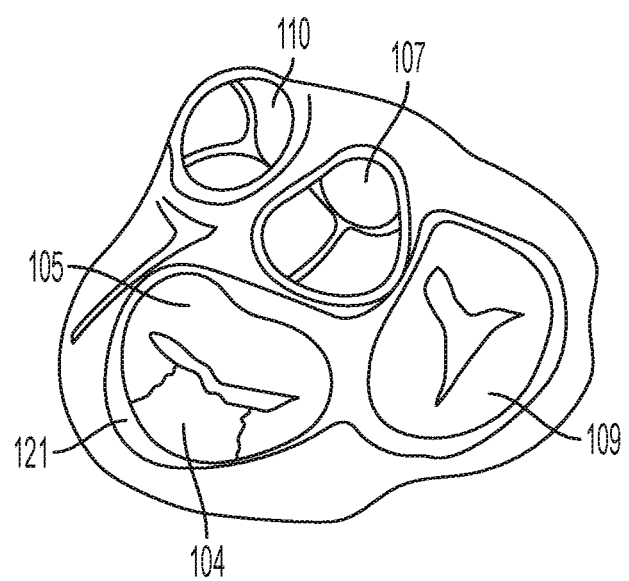
FIG. 1 depicts a short axis view of the heart in accordance with an embodiment.

This disclosure is not limited to the particular systems, devices, and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

When the term "valvular apparatus" is used in different variations, it may refer to the mitral valve apparatus and/or to the tricuspid valve apparatus and include the leaflets, the chordae, and/or the papillary muscles.

In an embodiment, an artificial chordae device is delivered to the target site, the mitral or tricuspid valve apparatus, through a catheter while the artificial chordae and their anchoring accessories are housed within a low diameter shaft which is correctly positioned and anchored to the functional configuration geometry and location. The catheter may be advanced to the target site through the vascular system. In an embodiment, the catheter may be advanced from the femoral vein or artery. In alternate embodiments, the catheter may be advanced from any blood vessel that allows access to the target site. In some embodiments the catheter may be advanced transapically, where a catheter is advanced through a small incision made in the chest wall and then through the apex. In some embodiments, the catheter may be advanced transatrially, where a catheter is advanced through a small incision made in the chest wall and then through the left or right atrium.

The artificial chordae device may include one or more of a variety of attachment methods for attachment to the native leaflet and myocardium. The artificial chordae device may include one or more of a variety of locking mechanisms between the leaflet capture subassembly and the native leaflet. In some embodiments, the artificial chordae device may include barbs to prevent rocking and device movement in relation to the leaflet upon insertion. The artificial chordae device may include one or more of a variety of tuning mechanisms. In addition, the artificial chordae device may include one or more of a variety of features that lock the tuning mechanism. Examples of the above-identified variations will be described further herein, although the described variations are illustrative only and are not meant to be limiting.

The illustrated example embodiments will be best understood by reference to the figures. The following description is intended only by way of example and illustrates certain example embodiments.

FIG. 1 depicts a short axis view of the heart displaying the four valves: the mitral valve 121, the tricuspid valve 109, the pulmonary valve 110, and the aortic valve 107. As shown, the mitral valve 121 includes the posterior leaflet 104 and the anterior leaflet 105, which will be discussed further herein in relation to various embodiments.

Figure 2:
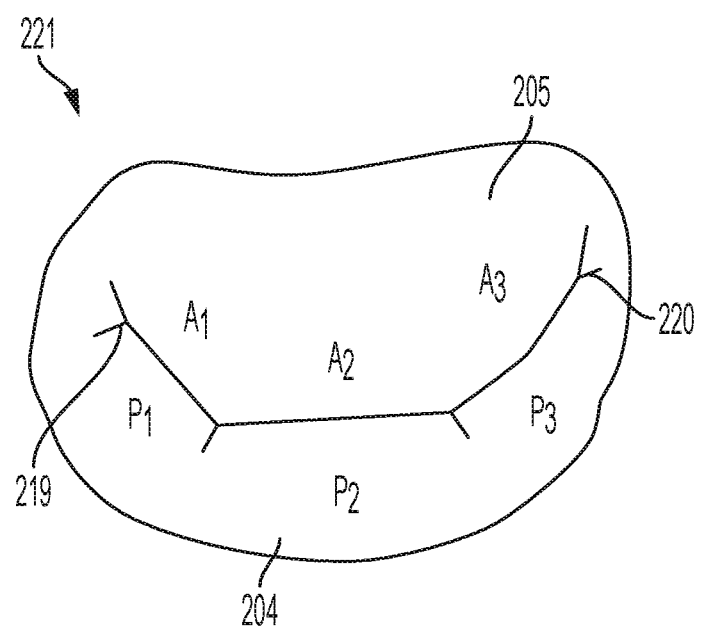
FIG. 2 depicts mitral valve leaflets of the heart in accordance with an embodiment.

FIG. 2 depicts a perspective of the mitral valve commonly known as the "surgical view" which identifies individual segments of the native leaflets of the mitral valve 221. As depicted in FIG. 2, individual segments (A1, A2, A3) of the anterior leaflet 205 and individual segments (P1, P2 and P3) of the posterior leaflet 204 are identified. The lateral commissure 219 and medial commissure 220 are also noted for reference.

Figure 3:
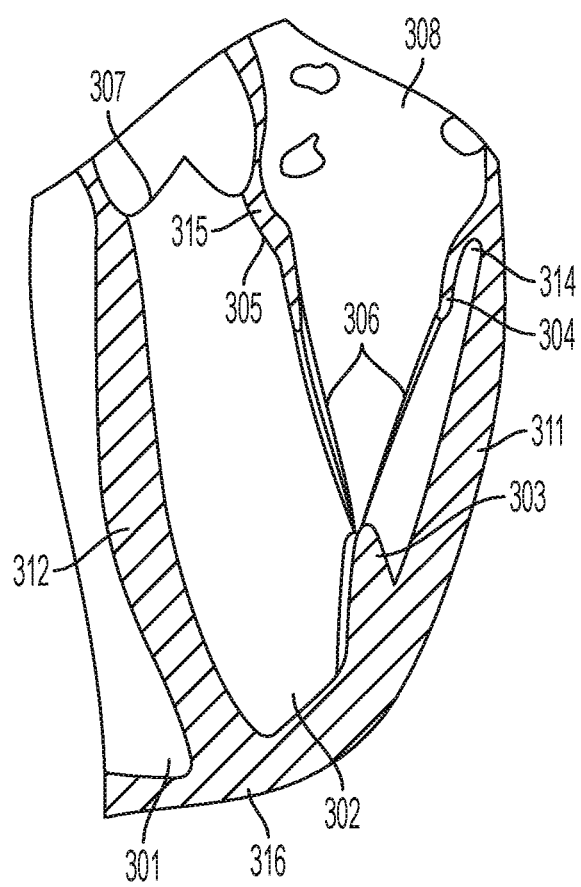
FIG. 3 depicts a long axis anterior to posterior view of the heart in accordance with an embodiment.

FIG. 3 depicts a left ventricular outflow tract view, anterior to posterior, of the heart which shows how the anterior 305 and posterior 304 leaflets are attached to the papillary muscles 303 by the chordae 306. FIG. 3 further depicts the left ventricle 302 and the right ventricle 301 separated by the intraventricular septum 312, the apex 316, the left atrium 308, and the aortic valve 307. Within the left ventricle 302, the posterior wall 311, mitral groove 314, and aortic-mitral continuity 315 are specifically identified.

Figure 4:
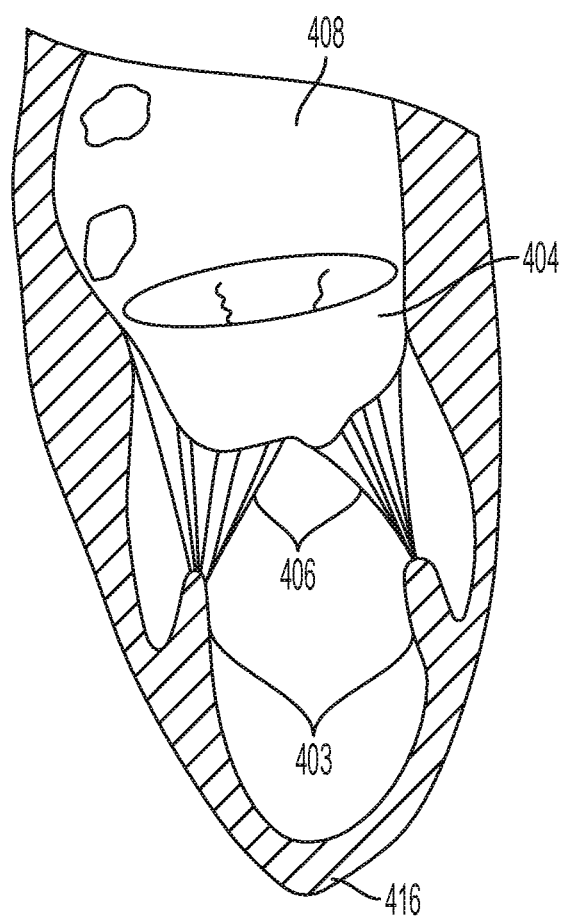
FIG. 4 depicts a long axis commissure to commissure view of the heart in accordance with an embodiment.

FIG. 4 depicts a perspective of the left side of the heart in commissure to commissure view showing the left atrium 408. Similar to FIG. 3, FIG. 4 depicts the attachment of the posterior leaflet 404 to the myocardium 403 via the chordae 406 near the apex of the heart 416.

Figure 5:
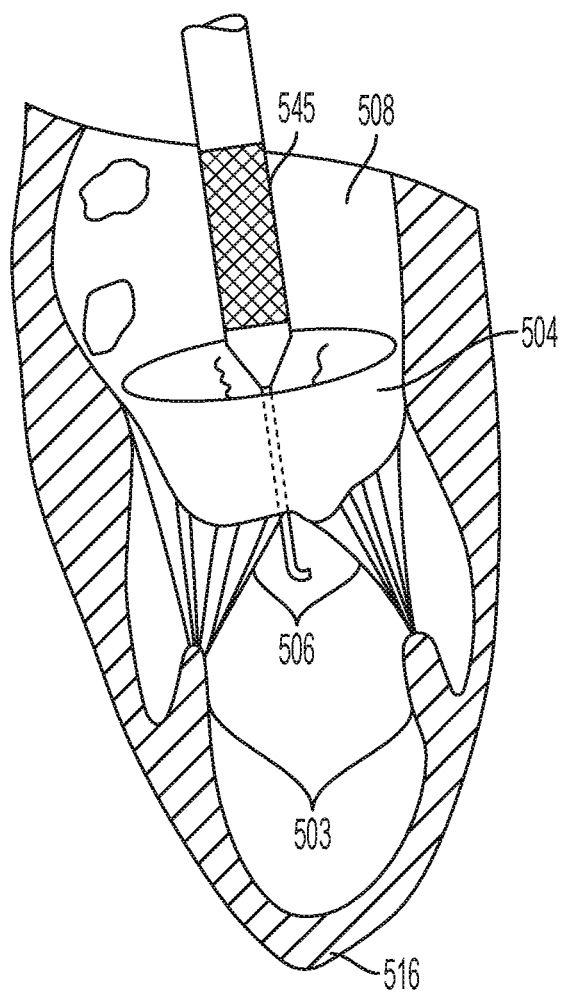
FIG. 5 depicts an illustrative transatrial approach in a commissure to commissure view of the heart in accordance with an embodiment.

FIG. 5 depicts an illustrative transatrial approach of a chordae repair device to the mitral valve apparatus in a commissure to commissure view of the heart in accordance with an embodiment. When using the transatrial approach, a catheter 545 is introduced into the left atrium 508 directly. In addition, the transatrial approach may pass by or cross-over the mitral valve and allow implantation of a chordae repair device between the posterior leaflet 504 and/or the papillary muscles 503 to repair the chordae 506.

Figure 6:
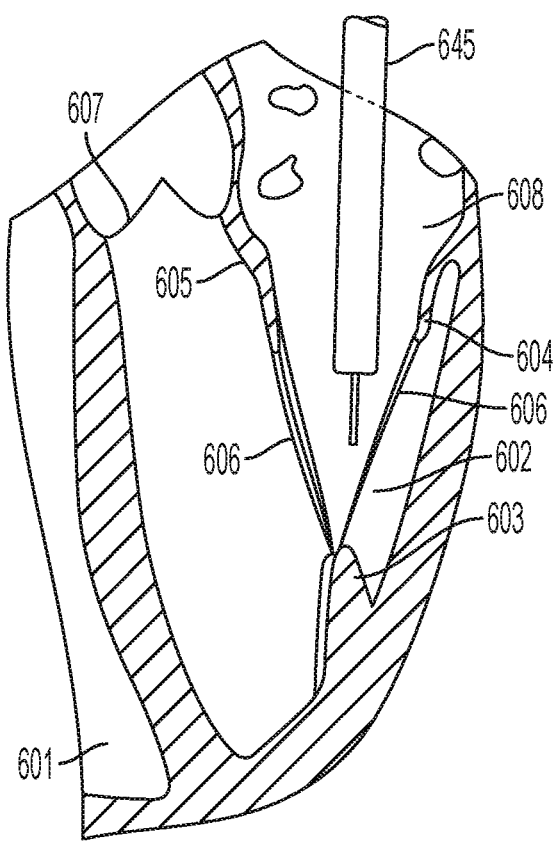
FIG. 6 depicts an illustrative transatrial approach in an anterior to posterior view of the heart in accordance with an embodiment.

FIG. 6 depicts an illustrative transatrial approach of a chordae repair device to the mitral valve apparatus in an anterior to posterior view of the heart in accordance with an embodiment. The catheter 645 is introduced into the left atrium 608 directly at the native valve comprising the anterior 605 and posterior 604 leaflets. Using this approach, implantation of aa chordae repair device may be made to the leaflets 604, 605 and the papillary muscles 603 in repair of the chordae 606 within the left ventricle 602. FIG. 6 further depicts the right ventricle 601 and aortic valve 607 for reference.

Figure 7:
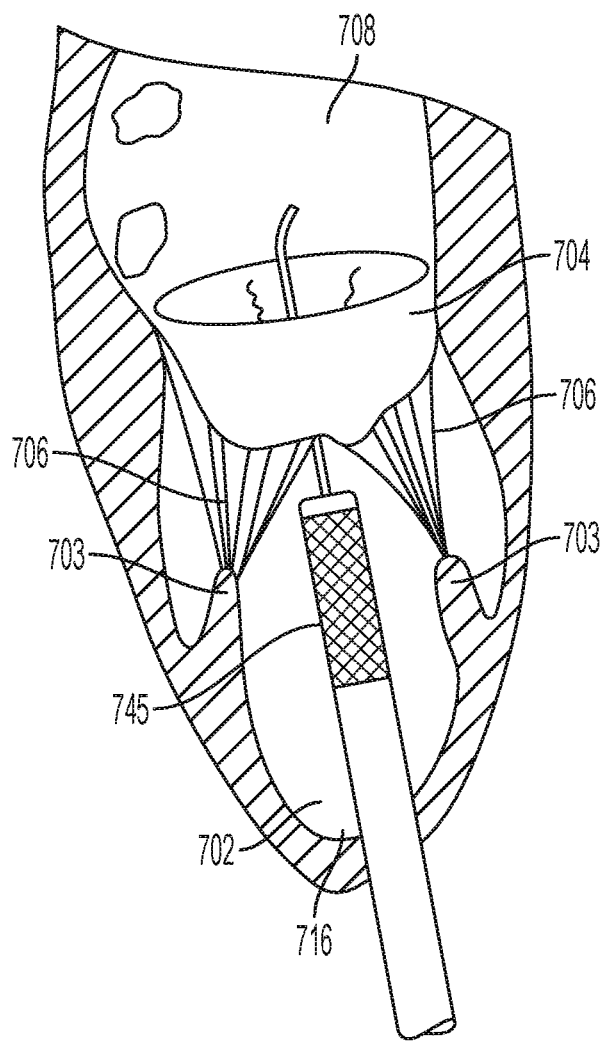
FIG. 7 depicts an illustrative transapical approach in a commissure to commissure view of the heart in accordance with an embodiment.

FIG. 7 depicts an illustrative transapical approach of a chordae repair device to the mitral valve apparatus in an anterior to posterior view of the heart in accordance with an embodiment. Using the transapical approach, the catheter 745 is introduced between the left atrium 708 and the ventricle 702. The transapical approach is a direct approach where the catheter 745 is introduced into the left ventricle across the apex 716 to allow implantation of the chordae repair device to the valvular apparatus to anchor between the leaflet 704 (e.g., posterior leaflet, interior leaflet, etc.) and the papillary muscles 703 to repair the chordae 706.

Figure 8:
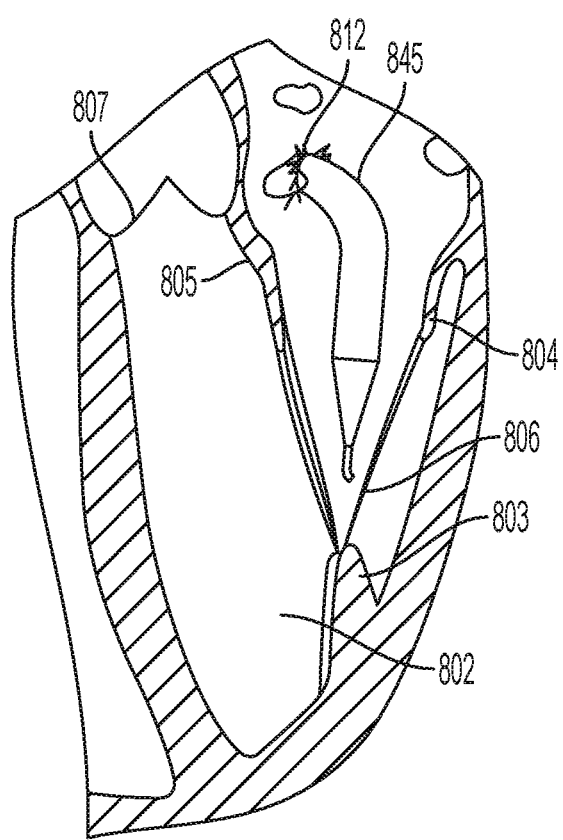
FIG. 8 depicts an illustrative transfemoral approach in an anterior to posterior view of the heart in accordance with an embodiment.

FIG. 8 depicts an illustrative transfemoral approach of the chordae repair device to the mitral valve apparatus in an anterior to posterior view of the heart in accordance with an embodiment. The transfemoral approach is a percutaneous approach where the catheter 845 is introduced into the femoral vein and advanced along the inferior vena cava to the right atrium, across the septum 812, to allow implantation of a chordae repair device to the valvular apparatus including the anterior 805 and posterior 804 leaflets, papillary muscles 803, and chordae 806. The aortic valve 807 is also shown for reference.

Figure 9:
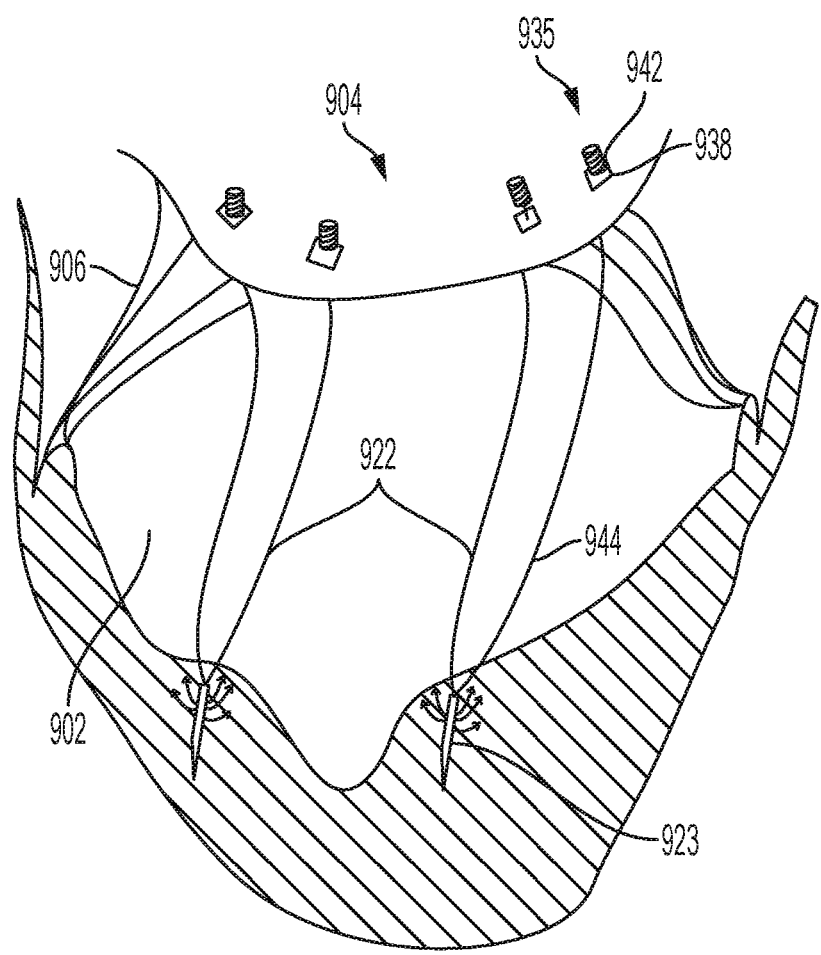
FIG. 9 depicts an illustrative posterior leaflet with a plurality of artificial chordae being implanted in accordance with an embodiment.

FIG. 9 depicts an illustrative posterior leaflet with a plurality of artificial chordae being implanted in accordance with an embodiment. As shown in FIG. 9, an artificial chordae device 922 is implanted at a plurality of locations on the posterior leaflet 904 of the left ventricle 902. The artificial chordae device 922 may be used to repair chordae 906 that failed due to, for example and without limitation, leaflet prolapse, flail, or other pathology. In some embodiments, the artificial chordae device 922 comprises a plurality of artificial chordae 944, an anchor subassembly 923 configured to attach to the myocardium, and a leaflet capture subassembly 935, with a tuning mechanism 942 and stress relief pad 938, configured to attach to the native leaflet. The implantation of one or more artificial chordae devices 922 may be performed serially or in parallel. Each artificial chordae device 922 may be tuned separately using the corresponding tuning mechanism 942. The one or more artificial chordae devices 922 may be visualized using, for example and without limitation, endoscopy, fluoroscopy, a CT scan, an MRI scan, and/or vital signals to assist in optimizing the result.

Figure 10:
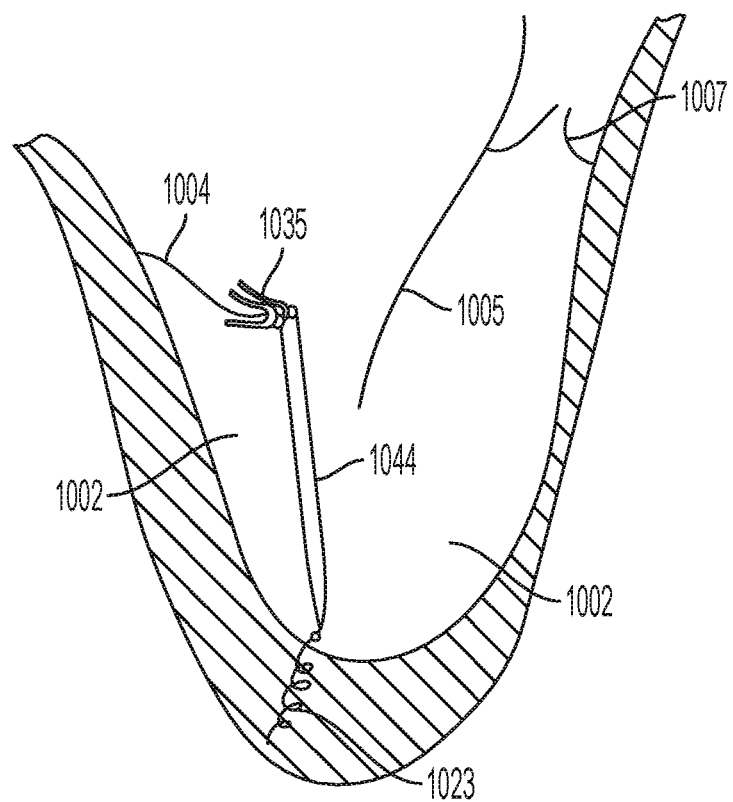
FIG. 10 depicts a side view of a posterior leaflet with an artificial chordae being implanted in accordance with an embodiment.

FIG. 10 depicts a side view of a posterior leaflet with an artificial chordae device being implanted in accordance with an embodiment. As shown in FIG. 10, one or more leaflet capture assemblies 1035 may be attached to the posterior leaflet 1004 in the left ventricle 1002 from a side view. The one or more leaflet capture assemblies 1035 may include a mechanism to ensure connectivity and proper tension. In some embodiments, the connectivity and tension may be tunable (e.g., separately or in combination) during and/or after deployment and attachment. An anchor assembly 1023 may be used to attach the artificial chordae 1044 to the myocardium. The anterior leaflet 1005 and aortic valve 1007 are shown for reference.

Figure 11:
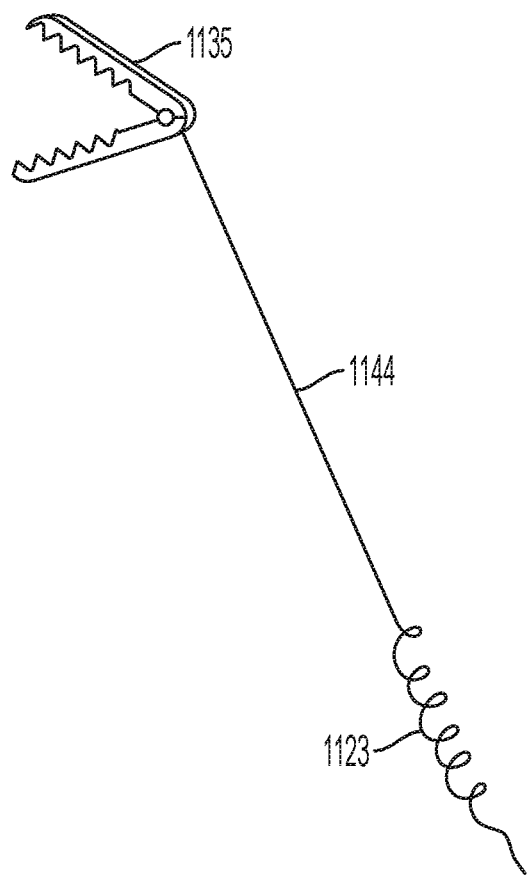
FIG. 11 depicts an illustrative artificial chordae with a leaflet capture mechanism in accordance with an embodiment.

FIG. 11 depicts an illustrative artificial chordae with a leaflet capture mechanism in accordance with an embodiment. An artificial chordae device comprises an artificial chordae 1144, a leaflet capture subassembly 1135, and an anchor subassembly 1123.

Figure 12:
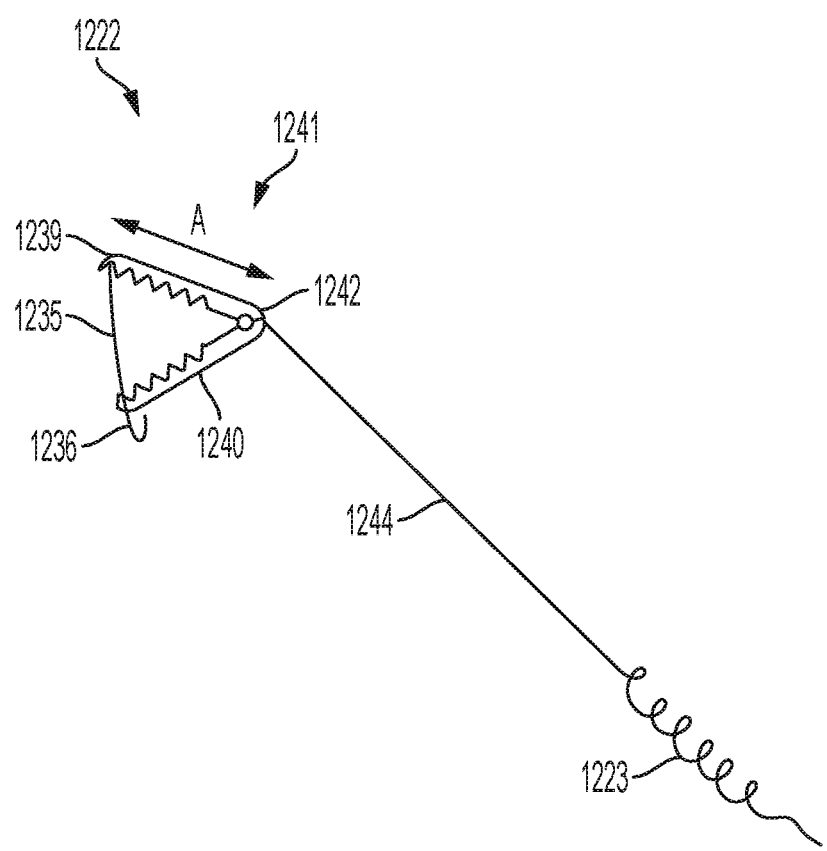
FIG. 12 depicts an illustrative open leaflet capture configuration on an artificial chordae in accordance with an embodiment.
Figure 13:
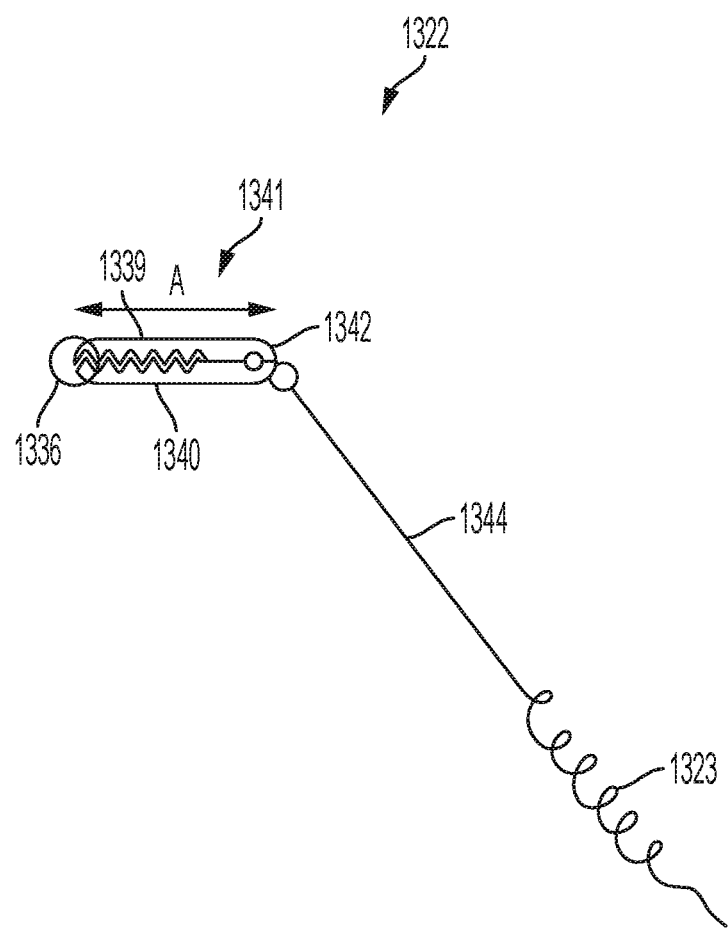
FIG. 13 depicts an illustrative closed leaflet capture configuration on an artificial chordae in accordance with an embodiment.

FIGS. 12 and 13 depict the leaflet capture subassembly 1235 of the artificial chordae, which is composed of an upper jaw 1239, a lower jaw 1240, and a lock feature 1236 to assure proper attachment to the native leaflet. The jaws 1239, 1240 capture the leaflet and have a depth of 2-8 mm, shown as dimension A 1241. In an embodiment, the geometry and the attachment depth of the jaws 1239, 1240 may be designed to prevent damage and unintentional detachment from the native leaflet. The artificial chordae 1244 may be attached to the jaws 1239, 1240 at the tuning mechanism 1242. The artificial chordae 1244 may be attached to a muscle using an anchor subassembly 1223. FIG. 12 depicts the artificial chordae 1244 with the leaflet capture subassembly 1235 in an open configuration.

FIG. 13 depicts the artificial chordae 1344 with the leaflet capture subassembly 1335 in a closed configuration. As shown in FIG. 13, the locking mechanism 1336 is engaged. As shown, dimension A 1341 represents the attachment depth of the leaflet capture subassembly 1335 to the native leaflet. In some embodiments, the tension of the artificial chordae 1344 may be adjusted at the tuning mechanism 1342. In some embodiments, the artificial chordae 1344 may be attached to a muscle using an anchor subassembly 1323.

Figure 14:
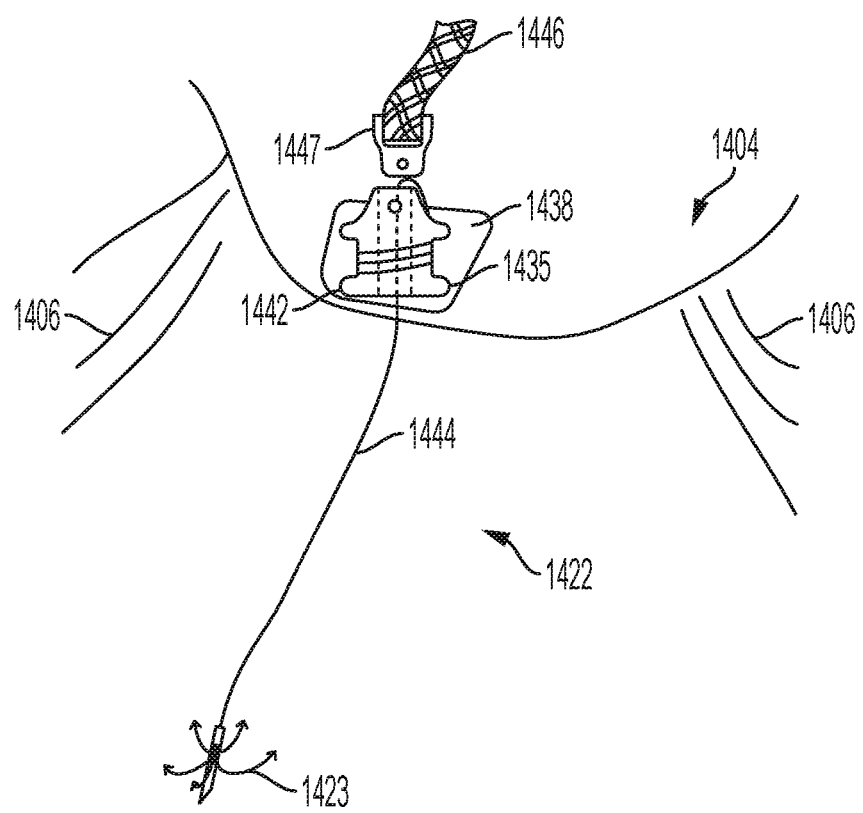
FIG. 14 depicts an illustrative pulley-based attachment and tuning mechanism in accordance with an embodiment.

FIG. 14 depicts an illustrative pulley-based attachment and tuning mechanism in accordance with an embodiment. As shown in FIG. 14, the artificial chordae device 1422 may include a pulley tuning mechanism. In some embodiments, the tuning mechanism may include a pulley 1442 that may be controlled by a torque cable 1446 resident in a delivery catheter. In some embodiments, the torque cable 1446 may be attached to the pulley 1442 via a connection feature 1447. In some embodiments, the leaflet capture assembly 1435 may include a stress relief pad 1438 that enables forces resulting from attachment to the native leaflet 1404 to be distributed. In such embodiments, distributing the attachment forces may prevent damage to the native leaflet 1404 and encapsulate the assembly 1435 after healing. In some embodiments, the artificial chordae 1444 may be attached to the muscle using a barbed anchor subassembly 1423. The artificial chordae 1444 may be tuned so that the artificial chordae replace the operation of the damaged chordae 1406.

Figure 15:
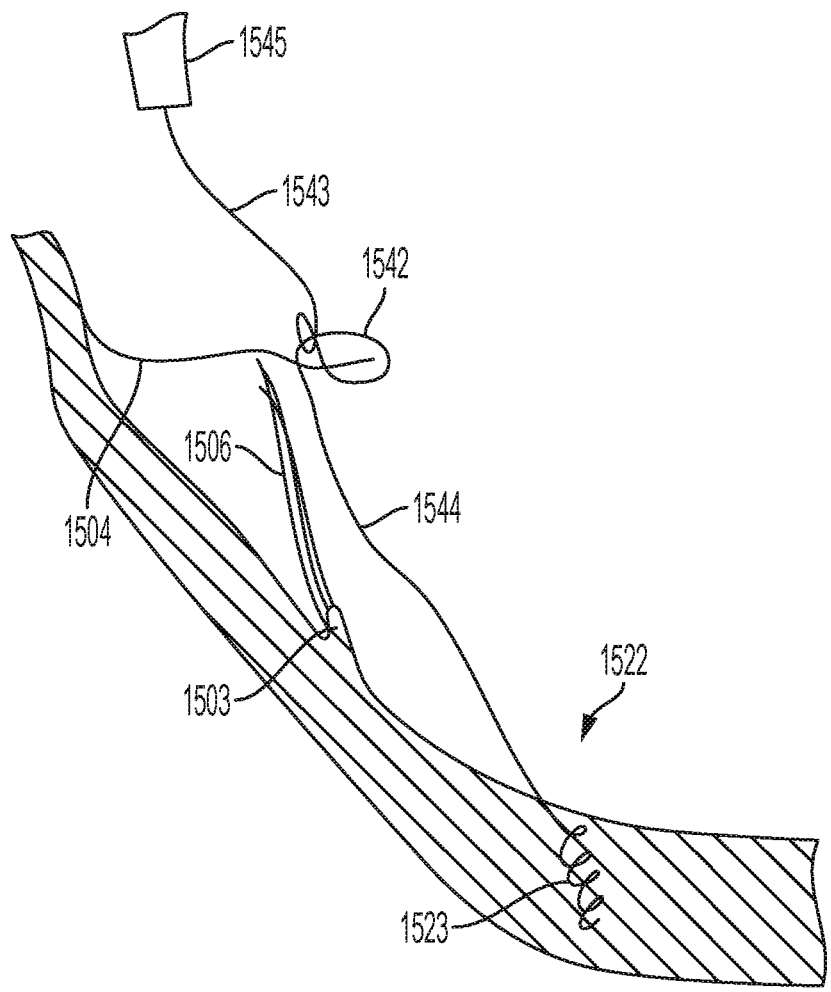
FIG. 15 depicts an illustrative knot-based attachment and tuning mechanism in accordance with an embodiment.

FIG. 15 depicts an illustrative knot-based attachment and tuning mechanism in accordance with an embodiment. As shown in FIG. 15, an artificial chordae device 1522 may include a tuning mechanism that includes a knot 1542. In some embodiments, the knot 1542 may be adjustable and may be used to tune the artificial chordae device 1522 to the correct length. In some embodiments, the knot 1542 may be tuned to the correct length through the delivery catheter 1545. In some embodiments, the knot 1542 may be locked to a final length through movement of a proximal section of a tightening suture 1543. In some embodiments, the artificial chordae device 1522 may be attached to the posterior leaflet 1504 and anchored via a screw-based anchor 1523 to the papillary muscles 1503 to repair the damaged chordae 1506.

Figure 16:
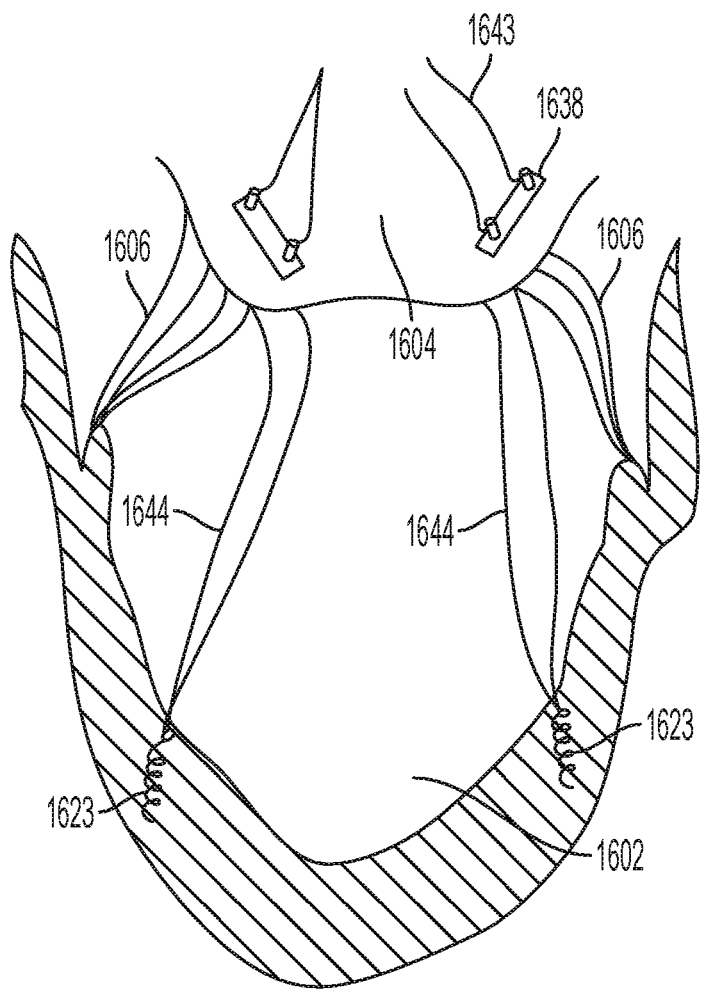
FIG. 16 depicts an illustrative knot-based attachment and tuning mechanism in accordance with an embodiment.

FIG. 16 depicts an illustrative knot-based attachment and tuning mechanism in accordance with an embodiment. As shown in FIG. 16, a plurality of artificial chordae 1644 are implanted in the left ventricle 1602 to properly repair the damaged chordae 1606. In some embodiments, each artificial chordae may be attached to the posterior leaflet 1604 via a suture 1643 and anchored to the myocardium via a screw-based anchor 1623. In some embodiments, the length of each of the artificial chordae 1644 may be adjusted independently by adjusting, for example, the corresponding knot-based tuning mechanism. In some embodiments, adjustments to the tuning mechanism may be performed from the delivery catheter.

In some embodiments, multiple devices may be attached to the posterior leaflet or the anterior leaflet. In such embodiments, an operator may control the distance between adjacent attachments to leaflet mechanisms. In another embodiment, one or more pads may be used for stress relief of the attachment. In some embodiments, the pads may be large patches that could support a plurality of attachment mechanisms 1638. In alternate embodiments, smaller patches may be used that only support a single mechanism 1638.

Figure 17:
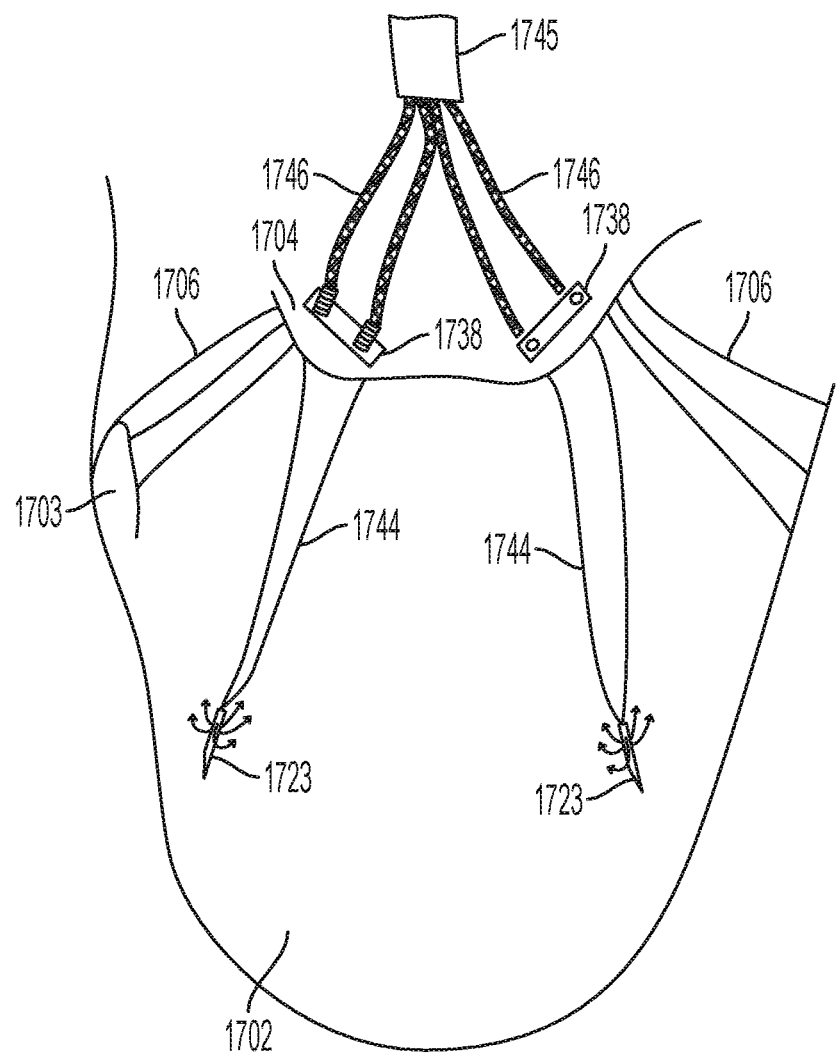
FIG. 17 depicts another illustrative anchor-based attachment and tuning mechanism in accordance with an embodiment.

FIG. 17 depicts another illustrative anchor-based attachment and tuning mechanism in accordance with an embodiment. As shown in FIG. 17, artificial chordae 1744 may be implanted to replace damaged chordae 1706 in the left ventricle 1702. In some embodiments, the artificial chordae 1744 may be attached to the posterior leaflet 1704 in pairs on stress relief pads 1738. In some embodiments, the artificial chordae 1744 may be anchored to the myocardium below the papillary muscles 1703. In some embodiments, the tuning mechanism may include one or more torque cables 1746 controlled via the delivery catheter 1745. In some embodiments, a barbed assembly 1723 may be used to anchor the artificial chordae 1744.

The length of each of the artificial chordae may be from about 20 mm to about 120 mm. For example, the length of an artificial chordae may be tuned to 20 mm, 30 mm, 40 mm, 50 mm, 60 mm, 70 mm, 80 mm, 90 mm, 100 mm, 110 mm, 120 mm, or to a length within a range between any two of these endpoints. The variation in the length of the artificial chordae may be used to address variations in ventricle size in a patient population as well as to allow the operator to make a decision as to where to anchor the assembly. For example, different operators may choose to anchor the assembly near to the apex, while other operators may choose to anchor the assembly near to the papillary muscle. Such decisions may be based on the anatomy of the patient and/or operator preference.

In some embodiments, the design of a chordae replacement device may allow loading the device into a low profile shaft having an outer diameter that is, for example, less than or equal to 13 mm. In some embodiments, the chordae replacement device and the associated delivery system may enable delivery of a plurality of devices, such as the leaflet capture assembly, anchor assembly, and artificial chordae. In some embodiments, the plurality of devices may be delivered consecutively or simultaneously. In some embodiments, the plurality of devices may be housed in parallel inside the catheter prior to delivery. In some embodiments, the plurality of devices may be housed consecutively within the catheter prior to delivery. In some embodiments, only one of the plurality of devices may be loaded into the catheter at a time. In some embodiments, the control mechanism (e.g., the torque cable 1746) may be retained within the catheter.

The leaflet capture assembly may be configured to attach to the native leaflets of the tricuspid valve or the mitral valve. When used in the mitral position, the leaflet capture assembly may lean in against the edges of the mitral leaflets, anterior or posterior, according to the area that requires treatment. In some embodiments, the attachment mechanism may enable tuning of the tension on the artificial chordae that attaches leaflets to the myocardium. In some embodiments, the attachment mechanism may enable precise positioning with respect to the leaflet. In some embodiments, the attachment mechanism may include a padded surface to distribute the forces and/or to encourage encapsulation of the assembly into the leaflet.

One of ordinary skill in the art will be aware that any combination of the various components described herein and equivalents may be used for the construction of a particular device based on this disclosure. In other words, the devices depicted herein are merely illustrative of the types of devices that may be constructed according to the teachings of this disclosure and are not meant to be limited to these illustrative embodiments.

Figure 18:
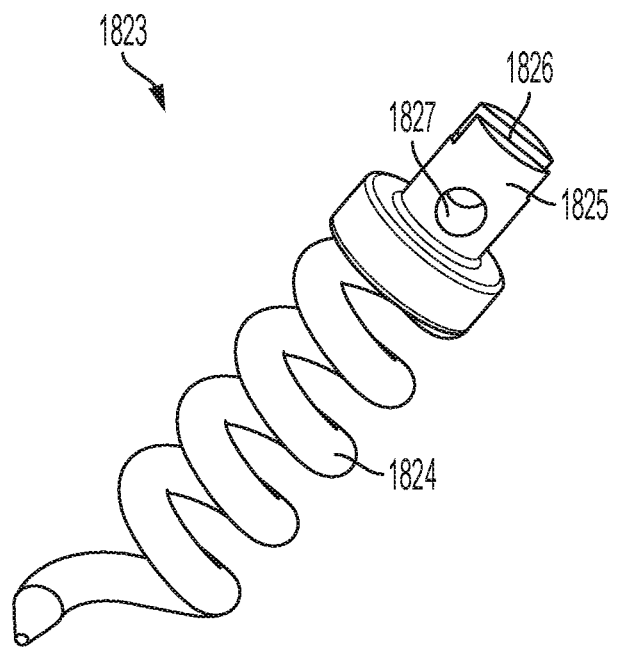
FIG. 18 depicts an illustrative anchor subassembly for an artificial chordae in accordance with an embodiment.

FIG. 18 depicts an illustrative anchor subassembly for an artificial chordae in accordance with an embodiment. The anchor assembly 1823 may be configured to attach to the myocardium. In some embodiments, the anchor assembly 1823 may include a self-expanding stent comprising a shape memory material (e.g., Nitinol). In some embodiments, the anchor assembly 1823 may be cut from a tube or sheet and/or use a pattern that allows crimping and expanding. In one embodiment, the anchoring assembly 1823 may be constructed from a wire formed into a coiled geometry configured to be screwed into the tissue. The coiled portion 1824 of the anchor assembly 1823 may be configured to penetrate into tissue and maintain an anchoring force during implantation and in vivo life expectancy.

In some embodiments, the anchor assembly 1823 may feature an interface portion 1825 that is configured to enable an attachment with a catheter during implantation. The interface portion 1825 may include an attachment 1826 to the delivery catheter that allows transmission of torque forces. The torque forces may be applied to the attachment 1826 to rotate the anchor assembly 1823 and enable the coiled portion 1824 to penetrate into tissue. In some embodiments, axial forces may also be applied to advance the anchor assembly 1823 into or retract the anchor assembly from tissue. In some embodiments, the interface portion 1825 may include one or more holes 1827 configured to attach artificial chordae to the anchor assembly 1823. Illustrative coil-based anchor assemblies are further depicted in FIGS. 10-13, 15, and 16.

Figure 19:
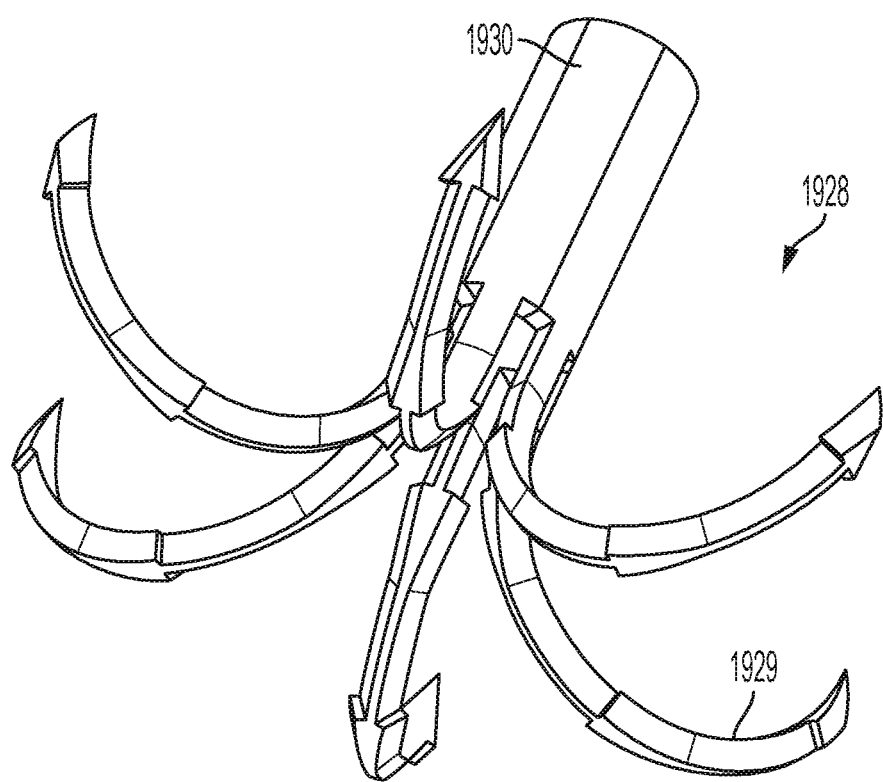
FIG. 19 depicts an illustrative inner member of an anchor subassembly in a deployed configuration in accordance with an embodiment.
Figure 20:
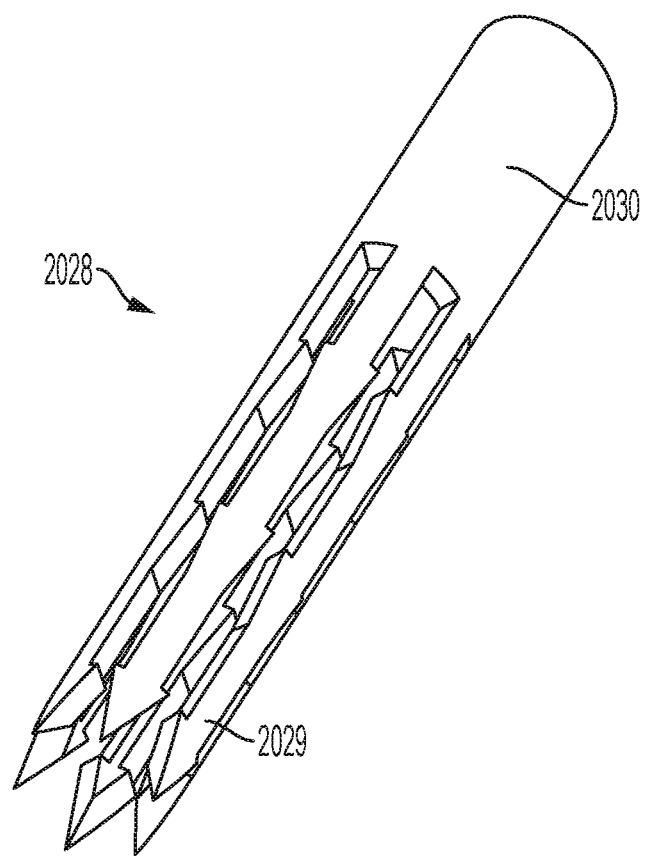
FIG. 20 depicts an illustrative inner member of an anchor subassembly in a non-deployed configuration in accordance with an embodiment.

FIG. 19 depicts an illustrative inner member of an anchor subassembly in a deployed configuration in accordance with an embodiment. In some embodiments, an anchor subassembly may include an outer member (depicted in FIG. 21) and an inner member 1928. The inner member may include a tube having a specific pattern that allows two different configurations as depicted in FIGS. 19 and 20. As shown in FIG. 19, a plurality of anchors 1929 may be positioned on a first end of the anchor subassembly 1928. The plurality of anchors 1929 may expand radially to anchor into tissue. In some embodiments, the opposite end 1930 of the anchor subassembly 1928 may provide an interface for attachment to the artificial chordae.

FIG. 20 depicts the illustrative inner member of the anchor subassembly of FIG. 19 in a non-deployed configuration. As shown in FIG. 20, the anchors 2029 of the anchor subassembly 2028 may be aligned parallel with the interface 2030 of the anchor subassembly. The anchor 2029 may be in the non-deployed configuration when housed within the outer member of the anchor subassembly as discussed further in reference to FIGS. 21 and 22.

In some embodiments, the inner member of the anchor subassembly may be constructed from one or more metals and/or an alloy. In one embodiment, the inner member is constructed from one or more metals that are biocompatible and are configured to permit the device to transform between the two configurations. For example, the inner member may comprise one or more of cobalt, chrome, stainless steel, or Nitinol.

Figure 21:
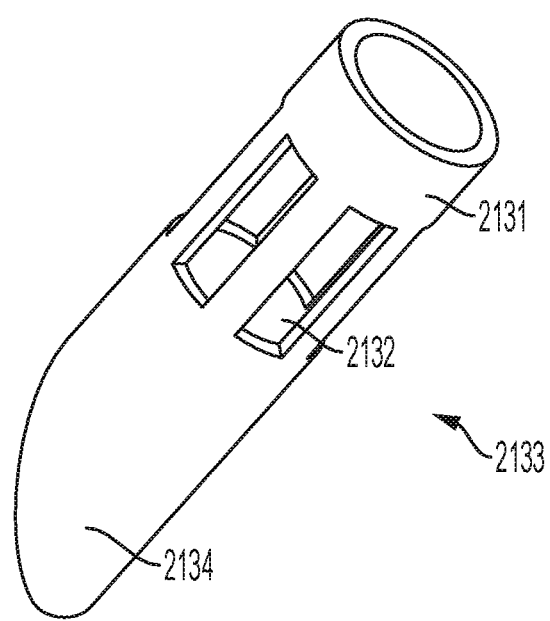
FIG. 21 depicts an illustrative outer member of an anchor subassembly in accordance with an embodiment.

FIG. 21 depicts an illustrative outer member of an anchor subassembly in accordance with an embodiment. As shown in FIG. 21, an outer member 2133 of an anchor assembly may comprise a tube with a plurality of windows 2132. In some embodiments, each of the plurality of windows may be located radially. Different window locations are contemplated within the scope of this disclosure. In some embodiments, the outer member 2133 may include a distal portion 2134 having a sharp edge. The sharp edge of the distal portion 2134 may be configured to enable the outer member to penetrate into tissue. In some embodiments, the outer member 2133 may further include a proximal section 2131. In some embodiments, the proximal section 2131 of the outer member 2133 may be used for attachment to the delivery system and/or to the artificial chordae.

In some embodiments, the outer member 2133 of the anchor subassembly may be constructed from one or more metals and/or an alloy. In one embodiment, the outer member 2133 is constructed from one or more metals that are biocompatible. For example, the outer member 2133 may comprise one or more of cobalt, chrome, stainless steel, or Nitinol. In some embodiments, the outer member 2133 may comprise a plastic, such as polyetheretherketone, other materials, or other combinations of materials that are biocompatible.

Figure 22:
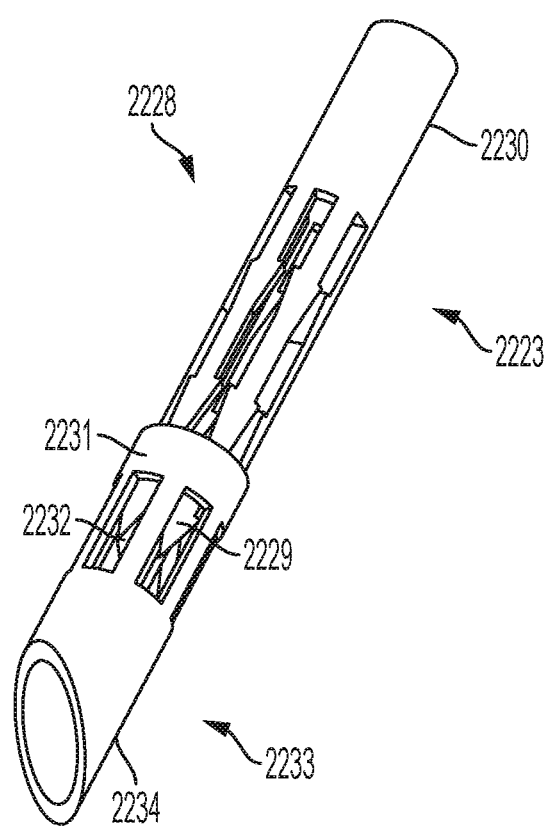
FIG. 22 depicts an illustrative anchor subassembly in a non-deployed configuration in accordance with an embodiment.
Figure 23:
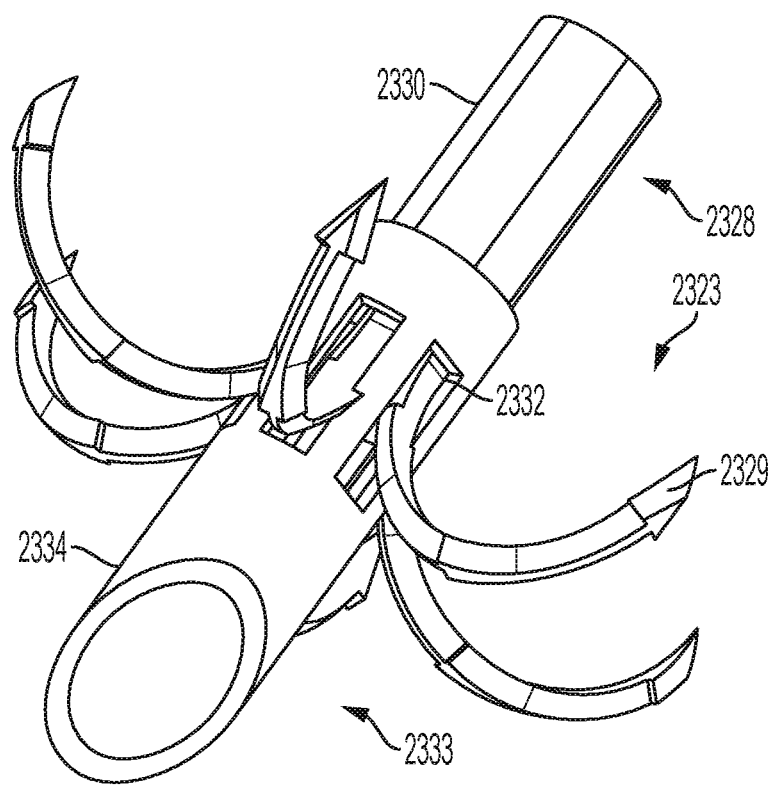
FIG. 23 depicts an illustrative anchor subassembly in a deployed configuration in accordance with an embodiment.

FIGS. 22 and 23 depict an illustrative anchor subassembly in a non-deployed configuration 2223 and a deployed configuration 2323, respectively, in accordance with an embodiment. In some embodiments, the inner member 2228/2328 may include a plurality of anchors 2229/2329 and the artificial chordae interface 2230/2330. In some embodiments, the inner member may be inserted into the outer member 2233/2333. In some embodiments, the outer member 2233/2333 may include a plurality of anchor windows 2232/2332, a control interface 2231 to the delivery system, and a distal end 2234/2334.

In some embodiments, transitioning between the non-deployed configuration and the deployed configuration may be controlled via the delivery catheter by advancing, retracting, and/or rotating the catheter. In some embodiments, transitioning between the two configurations may further be performed with the outer member. For example, linear movement of the inner member 2228/2328 with respect to the outer member 2233/2333 may cause the plurality of anchors 2229/2329 to transition between the two configurations. In some embodiments, movement of the inner member 2228/2328 may cause the outer member 2233/2333 to deflect the anchors through the windows 2232/2332 mechanically. In some embodiments, the inner member 2228/2328 may be manufactured from a shape memory material, such as Nitinol, and movement of the inner member with respect to the outer member 2233/2333 may cause the anchors to transition to the deployed configuration. In some embodiments, the control interface 2231 may be designed to allow an easy and safe release after the device is anchored to the tissue.

In some embodiments, the inner member may be manufactured by machining, grinding, and/or laser cutting. In some embodiments, the distal ends 2234/2334 of the anchors 2229/2329 may be sharpened or grinded to enable tissue penetration. In some embodiments, the anchors 2229/2329 may be aligned in a specific direction. In some embodiments, the anchors 2229/2329 may be aligned in two opposing directions. In some embodiments, the anchors 2229/2329 may be aligned in a plurality of directions.

Any number of anchors 2229/2329 may be used within the scope of this disclosure. In some embodiments, the distal ends 2234 may be inside the corresponding windows 2232 to assure deployment through the windows when the inner member 2228 is within the outer member 2233 in the non-deployed configuration. In some embodiments, the inner member 2228 may be stored within the catheter and advanced into the outer member 2233 separately. In some embodiments, the inner diameter of the outer member 2233 may be in a range of about 0.8 mm to about 4 mm. In some embodiments, the outer diameter of the inner member 2228 may be in a range of about 0.8 mm to about 4 mm, but in any event is less than the inner diameter of the outer member 2233 to allow movement of the inner member therein.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A method of repairing a native chordae of a patient using an artificial chordae, the method comprising:
   inserting the artificial chordae into the patient using a delivery system, wherein the artificial chordae is inserted in a non-deployed configuration;
   delivering the artificial chordae to a desired position within the patient;
   causing the artificial chordae to transition from the non-deployed configuration to a deployed configuration;
   anchoring the artificial chordae to a myocardium of the patient via an anchoring assembly comprising an inner member comprising a barbed anchor and an outer member comprising a plurality of windows, the inner member positioned within the outer member;
   attaching the artificial chordae to a leaflet of the native chordae at an attachment location via a leaflet capture subassembly coupled to the artificial chordae, the leaflet capture subassembly comprising an upper jaw and a lower jaw configured lock the leaflet between the upper jaw and the lower jaw; and
   tuning the artificial chordae to a desired tension,
   wherein the artificial chordae is anchored to the myocardium by deploying the barbed anchor of the inner member through the plurality of windows of the outer member and into the myocardium to secure the artificial chordae to the myocardium.

2. The method of claim 1, further comprising delivering one or more additional devices to the desired position.

3. The method of claim 2, wherein the one or more additional devices comprise the anchoring assembly and the leaflet capture subassembly.

4. The method of claim 2, wherein the artificial chordae and the one or more additional devices are delivered via a single catheter.

5. The method of claim 2, wherein the artificial chordae and the one or more additional devices are delivered in parallel within a single catheter.

6. The method of claim 2, wherein the artificial chordae and the one or more additional devices are delivered in series within a single catheter.

7. The method of claim 2, further comprising tuning the one or more additional devices and the artificial chordae simultaneously.

8. The method of claim 1, further comprising installing a stress relief pad at the attachment location on the leaflet of the native chordae, wherein the stress relief pad is configured to lower stress on the leaflet and assist in healing thereof.

9. The method of claim 8, further comprising delivering one or more additional devices to the desired position, wherein the artificial chordae and the one or more additional devices are configured to share use of the stress relief pad.

10. The method of claim 1, wherein the artificial chordae is tuned via a tuning mechanism, the tuning mechanism comprising a pulley interfaced to a torque cable.

11. The method of claim 1, wherein the artificial chordae is tuned via a tuning mechanism, the tuning mechanism comprising a knot in a tightening suture that is configured to be adjusted to a desired length and locked to the desired length through movement of a proximal section of the tightening suture.

12. The method of claim 1, wherein the barbed anchor is configured to be delivered to an anchoring location in a non-deployed configuration and then deployed radially into a tissue of the myocardium to secure the artificial chordae thereto.

13. The method of claim 12, wherein the outer member is configured to:
  lock the barbed anchor in place during delivery; and
  control deployment of the barbed anchor through movement of the delivery system.

* * * * *